(12) United States Patent  (10) Patent No.: US 9,192,788 B2
Vahala et al.  (45) Date of Patent: Nov. 24, 2015

(54) THERAPEUTIC APPARATUS, COMPUTER PROGRAM PRODUCT, AND METHOD FOR DETERMINING AN ACHIEVABLE TARGET REGION FOR HIGH INTENSITY FOCUSED ULTRASOUND

(75) Inventors: Erkki Tapani Vahala, Hyvinkaa (FI); Marko Tapani Hakkinen, Espoo (FI)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/979,896

(22) PCT Filed: Jan. 12, 2012

(86) PCT No.: PCT/IB2012/050152
§ 371 (c)(1),
(2), (4) Date: Jul. 16, 2013

(87) PCT Pub. No.: WO2012/098482
PCT Pub. Date: Jul. 26, 2012

(65) Prior Publication Data
US 2013/0296742 A1  Nov. 7, 2013

(30) Foreign Application Priority Data

Jan. 18, 2011 (EP) .................................... 11151213

(51) Int. Cl.
*A61H 1/00* (2006.01)
*A61N 7/02* (2006.01)
*A61B 19/00* (2006.01)

(52) U.S. Cl.
CPC . *A61N 7/02* (2013.01); *A61B 19/50* (2013.01); *A61B 2019/5236* (2013.01)

(58) Field of Classification Search
CPC ... A61N 7/02; A61B 19/50; A61B 2019/5236
See application file for complete search history.

(56) References Cited

U.S. PATENT DOCUMENTS 5,553,618 A * 9/1996 Suzuki et al. ................. 600/411
6,241,670 B1 6/2001 Nambu
(Continued)

FOREIGN PATENT DOCUMENTS

| EP | 2165737 A1 | 3/2010 |
|----|------------|--------|
| WO | 2009045411 A2 | 4/2009 |
| WO | 2010043621 A1 | 4/2010 |

OTHER PUBLICATIONS

Hamza-Lup et al., Online External Beam Radiation Treatment Simulator. Int J CARS, 2008, vol. 3; pp. 275-281.*

*Primary Examiner* — James Kish

(57) ABSTRACT

A therapeutic apparatus comprising a high intensity focused ultrasound system for treating a target region. The therapeutic apparatus further comprises a display for displaying treatment planning data. The therapeutic apparatus further comprises a memory containing machine executable instructions. The memory further contains a geometric model of the high intensity focused ultrasound system. Execution of the instructions causes a processor to receive the treatment planning data. Execution of the instructions causes the processor to render the geometric representation of the target region from the treatment planning data on the display. Execution of the instructions further causes the processor to calculate an achievable target region using the geometric model. Execution of the instructions further causes the processor to render the achievable target region on the display.

15 Claims, 5 Drawing Sheets

(56) References Cited

U.S. PATENT DOCUMENTS

| | | |
|---|---|---|
| 6,512,942 B1 | 1/2003 | Burdette |
| 6,582,381 B1 * | 6/2003 | Yehezkeli et al. ............... 601/2 |
| 6,914,959 B2 | 7/2005 | Bailey |
| 7,453,983 B2 | 11/2008 | Schildkraut et al. |
| 7,699,780 B2 * | 4/2010 | Vitek et al. ................... 600/439 |
| 7,773,788 B2 | 8/2010 | Lu |
| 8,287,471 B2 * | 10/2012 | Liu et al. ........................... 601/3 |
| 8,725,232 B2 * | 5/2014 | Vahala et al. ................. 600/411 |
| 2003/0109780 A1 * | 6/2003 | Coste-Maniere et al. .... 600/407 |
| 2004/0009459 A1 * | 1/2004 | Anderson et al. ............. 434/262 |
| 2005/0234327 A1 * | 10/2005 | Saracen et al. ................ 600/407 |
| 2005/0251029 A1 | 11/2005 | Khamene et al. |
| 2005/0283097 A1 | 12/2005 | Weintraub |
| 2006/0058671 A1 * | 3/2006 | Vitek et al. ................... 600/447 |
| 2007/0156123 A1 * | 7/2007 | Moll et al. ........................ 606/1 |
| 2007/0219448 A1 * | 9/2007 | Seip et al. ..................... 600/454 |
| 2008/0116351 A1 * | 5/2008 | Dave et al. .................... 248/646 |
| 2008/0161677 A1 * | 7/2008 | Sutherland et al. ........... 600/417 |
| 2008/0200806 A1 * | 8/2008 | Liu et al. ....................... 600/439 |
| 2008/0242969 A1 * | 10/2008 | Sayeh et al. .................. 600/407 |
| 2008/0312561 A1 * | 12/2008 | Chauhan ........................... 601/2 |
| 2009/0088623 A1 * | 4/2009 | Vortman et al. .............. 600/411 |
| 2010/0030076 A1 * | 2/2010 | Vortman et al. .............. 600/439 |
| 2010/0063496 A1 | 3/2010 | Trovato et al. |
| 2010/0125192 A1 * | 5/2010 | Chopra et al. ................ 600/411 |
| 2010/0204828 A1 * | 8/2010 | Yoshizawa et al. ........... 700/245 |
| 2010/0222676 A1 | 9/2010 | Ogihara et al. |
| 2011/0137147 A1 * | 6/2011 | Skliar et al. .................. 600/411 |
| 2011/0208055 A1 * | 8/2011 | Dalal et al. ................... 600/439 |
| 2011/0270136 A1 * | 11/2011 | Vitek et al. ....................... 601/2 |
| 2012/0053597 A1 * | 3/2012 | Anvari et al. ................. 606/130 |
| 2012/0150035 A1 * | 6/2012 | Seip et al. ..................... 600/439 |
| 2013/0035582 A1 * | 2/2013 | Radulescu et al. ............ 600/411 |
| 2013/0131495 A1 * | 5/2013 | Konofagou et al. .......... 600/411 |
| 2013/0144194 A1 * | 6/2013 | Ahn et al. ......................... 601/3 |

\* cited by examiner

THERAPEUTIC APPARATUS, COMPUTER PROGRAM PRODUCT, AND METHOD FOR DETERMINING AN ACHIEVABLE TARGET REGION FOR HIGH INTENSITY FOCUSED ULTRASOUND

TECHNICAL FIELD

The invention relates to high intensity focused ultrasound, in particular to the determination of an achievable target region which may be sonicated by the high intensity focused ultrasound system.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures.

To selectively treat tissue, a focused ultrasonic transducer can be used to focus the ultrasound on a particular treatment or target volume. The transducer is typically mounted within a medium, such as degassed water, that is able to transmit ultrasound. Actuators are then used to adjust the position of the ultrasonic transducer and thereby adjust the tissue region that is being treated.

SUMMARY OF THE INVENTION

The invention provides for a therapeutic apparatus, a computer program product, and a method in the independent claims. Embodiments are given in the dependent claims.

A difficulty when planning high intensity focused ultrasound (HIFU) therapy is determining whether a particular point or region within a subject can be sonicated by the high intensity focused ultra sound system. The Achievable Target Area (ATA), as used here, encompasses a two-dimensional area that can potentially be sonicated by the high intensity focused ultrasound system. The Achievable Target Volume (ATV) encompasses a volume that can potentially be sonicated by the high intensity focused ultrasound system. ATA and ATV are related: that is, ATA is an intersection area of a slice of a subject and the ATV in the said subject. ATV corresponds to the real treatment volume of finite dimensions, but in many cases ATA is more practical for planning purposes due to presentational clarity on two-dimensional displays.

Presently, the state of the art in ATA calculations is based on iterative or analytical solutions to directly calculate ATA contours on an arbitrary slice. The state of the art in ATV calculations is based either on predetermined rough estimates of the volume or pre-calculated volumes for number of degree of freedom variations.

Iterative solutions for ATA calculation are typically slow and prevent instant feedback for interactive work. Analytical solutions succeed only for a small subset of possible mechanical devices and are difficult to update when mechanics or characteristics of the device change. Embodiments of the invention may solve this problem and other by performing Gradual ATA calculations, which provide an immediate, coarse result for interactive work and, later on, accurate results for detailed examination of the slice or volume. Tessellation-based collision tests are easy to adapt to modifications in the HIFU device and its surroundings.

Another difficulty with the state of the art is that predetermined rough ATV model provides inaccurate volume that can only be presented as an estimate of the volume due to possibly large errors in the border areas of the volume. Pre-calculated volumes can require a lot of calculation resources and resulting data set can be large and the accuracy of the resulting volume depends on the amount of degree of freedom variations the pre-calculation was performed with.

Fast visualization of Achievable Target Area (ATA) on an arbitrary two-dimensional slice and/or Achievable Target Volume (ATV) would be beneficial for intraprocedural high-intensity focused ultrasound (HIFU) therapy. Attempts to analytically solve ATA/ATV regions based on the robotics and electro-acoustic characteristics of a HIFU device are difficult, error prone, and laborious due to large number of variables and degree of freedoms involved.

In some embodiments, ATA/ATV regions are defined by gradually filling the target slice/volume with increasingly accurate areas the HIFU device is able to reach, and where each area is produced from a valid single point calculated from stochastically, quasi-stochastically, or deterministically varied degrees of freedom and variables of the device and its environment.

In some embodiments, the check to determine whether a point on the slice/volume is valid device position is calculated with collision tests of tessellated surface models of the HIFU device and its surroundings, reducing the checks for collision into simple tests of intersections between tessellation primitives.

In some embodiments, the tessellated surfaces can be functions of degrees of freedom and/or other variables being stochastically or deterministically varied.

In some embodiments, the electro-acoustic characteristics of the HIFU device are approximated with a far-field shapes, whose collisions with surroundings or unwanted tissue areas or volumes can be used to modify or invalidate an otherwise mechanically and electro-acoustically acceptable degrees of freedom.

Embodiments of the invention may provide a method for rapidly estimating the achievable target area/volume, while still being accurate for detailed work. The method is easily adaptable to new and altered HIFU device configurations.

In some embodiments, ATA/ATV regions are defined by randomizing or deterministically testing the non-fixed degrees of freedom of a HIFU device—both the mechanical and electrical offsets. The values are fed into the collision test algorithm. If the algorithm deems the values valid, the area surrounding the point is visualized as being part of the ATA/ATV.

The initial degrees of freedom can be either derived from the allowed ranges of the HIFU device, or the whole slice/volume can be sparsely populated with points and each point is then used to calculate degrees of freedom of the HIFU device by back-projecting the device from its focal point (the point in slice/volume). These initial values can be further reduced by fast calculations, such as sanity checks against known maximum values for the degrees of freedom. This way the number of computationally more expensive collision tests can be reduced. If back-projection is used, subsequent rounds add points in interstitial space of the grid, whereas forward projection expands the allowed area/volume. In both cases the accuracy improves gradually.

In another embodiment, the check to determine whether a point on the slice is valid device position is calculated with collision tests of triangle-tessellated surface models of the HIFU device and its surrounding mechanical box, reducing the checks for collision into simple tests of intersections between triangles. Surface models do not have to model the mechanics exactly; models can also contain features that provide additional limitations to/relax the collision checks. In addition to the collision check, device model can also contain other limitations to further limit the HIFU device movement, e.g., in the form of minimum and maximum values for the degrees of freedom.

In another embodiment, the tessellated surfaces of the HIFU device are calculated from the mechanical degrees of freedom. HIFU device model can model movement of individual parts of the mechanics, thus taking into account collisions of individual parts like arms and levers.

In another embodiment, the electro-acoustic characteristics of the HIFU device are approximated with a far-field shapes, such as cones, whose collisions with surroundings or unwanted tissue areas or volumes can be used to invalidate or modify an otherwise mechanically and electro-acoustically acceptable degrees of freedom.

Besides being applicable for planning HIFU therapy, the invention is also relevance to other, minimally invasive treatment methods, where the degrees of freedom of the robotic device are limited by its surroundings.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, parallel port, IEEE 1284, serial port, RS-232 port, IEEE-488 port, Bluetooth connection, Wireless local area network connection, TCP/IP connection, Ethernet connection, control voltage interface, MIDI interface, analog input interface, and digital input interface.

'Magnetic Resonance (MR) data' as used herein encompasses the recorded measurements of radio frequency signals emitted by atomic spins by the antenna of a Magnetic resonance apparatus during a magnetic resonance imaging scan.

A 'Magnetic Resonance image' as used herein encompasses the reconstructed two or three dimensional visualization of anatomic data contained within the magnetic resonance imaging data. This visualization can be performed using a computer and may be displayed on a display. A magnetic resonance image is a type of medical image. A 'medical image' as used herein is an image comprising a visualization of anatomic data or which is descriptive of one or more anatomic structures.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a therapeutic apparatus comprising a high-intensity focused ultrasound system for treating a target region of a subject. The high-intensity focused ultrasound system may treat the target region by heating or ablating tissue within the target region. The therapeutic apparatus further comprises a processor for controlling the therapeutic system. The therapeutic apparatus further comprises a display for displaying treatment planning data. The treatment planning data as used herein encompasses data which is descriptive of instructions or plans for operating a high-intensity focused ultrasound system for treating the target region. The therapeutic apparatus further comprises a memory containing machine executable instructions for execution by the processor. The processor may be located within a computer system. If the processor refers to multiple processors the processors may be distributed amongst multiple computer systems. Additionally the processor may also be contained within a controller. The memory further contains a geometric model of the high-intensity focused ultrasound system.

Execution of the instructions causes the processor to receive the treatment planning data. The treatment planning data comprises a geometric representation of the target region. The display may in some embodiments only display a portion of the treatment planning data. For instance only the geometric representation may be rendered on the display. Execution of the instructions further causes the processor to render the geometric representation of the target region on the display. In some embodiments the geometric representation is displayed with other data or information. For instance the geometric representation of the target region may be displayed adjacent to or superimposed upon a medical image of the subject.

Execution of the instructions further causes the processor to calculate an achievable target region in accordance with the geometric model. The achievable target region may be representative of a volume or an area. The achievable target region is representative of a region treatable by the high-intensity focused ultrasound system. The high-intensity focused ultrasound system may comprise an ultrasonic transducer for focusing ultrasound into a sonication point for treating the target region or a portion of the target region. Typically the ultrasound is steered by a combination of electrical and/or mechanical means. As such the high-intensity focused ultrasound system is only able to treat regions allowable by its mechanical motion and electronic beam steering. The achievable target region is a region of the subject which can be treated by the high-intensity focused ultrasound system. The calculation of the achievable target region may also be interpreted as to estimate the achievable target region. In some embodiments the achievable target region is calculated or estimated by choosing test sonication points. As a larger number of points are used the accuracy of the estimate of the achievable target region improves.

Execution of the instructions further causes the processor to render the achievable target region on the display. This embodiment may be advantageous because the achievable target region is superimposed on the geometric representation of the target region. An operator or user of the therapeutic apparatus can therefore easily see if the target region could be treated by the high-intensity focused ultrasound system.

In another embodiment the high-intensity focused ultrasound system comprises an ultrasound transducer. The high-intensity focused ultrasound system further comprises a mechanical positioning system. The mechanical positioning system may be adapted for mechanically positioning the ultrasound transducer. The high-intensity focused ultrasound system may contain actuators and linkages for mechanically positioning the ultrasound transducer. The geometric model is descriptive of the mechanical structure of the ultrasound transducer and the mechanical positioning system. As used herein a geometric model encompasses a model which describes the three-dimensional shape of an object. This embodiment is advantageous because the geometric model describes the mechanical structure of the ultrasound transducer and the mechanical positioning system. This may be used to calculate the possible locations and positions of the ultrasound transducer. This allows the determination of locations that can be sonicated or treated by the ultrasound transducer.

In another embodiment the geometric model comprises a geometric representation of the path of focused ultrasound generated by the ultrasound transducer. This is particularly advantageous because sonication points may be determined using a geometric model. Ultrasonic transducers are typically parabolic or are at least concave shaped. This allows ultrasonic energy to be focused into specific points or volumes. The ultrasonic energy can then be represented by a geometric shape which represents the path of the ultrasound. For instance from a concave shape a cone or similar shape may be used to make a representation of the path of ultrasound. This is advantageous because the sonication points can be very rapidly determined by using a purely geometric model. The path of the ultrasound does not need to be calculated because it is approximated using the geometric representation.

In another embodiment the achievable target region is calculated by the execution of instructions which cause the processor to select at least one sonication point. The achievable target region is calculated further by the execution of instructions which cause the processor to calculate the position of the ultrasound transducer and the mechanical positioning system which allow sonication of the at least one sonication point in accordance with the geometric model. Since the geometric model is descriptive of the structure of the mechanical positioning system and the ultrasonic transducer the ultrasound transducer and mechanical positioning system can be assembled into a model which can then be used to calculate if the position is able to be sonicated or not.

In another embodiment the allowance of sonication is tested using a collision test in accordance with the geometric model. This may be achieved for instance by choosing a sonication point and then positioning the ultrasonic transducer in one or more positions such that that point is sonicated. The ultrasound transducer can then be tested to see if it is within the mechanical boundaries which are allowed for the ultrasound transducer. For instance if a sonication point is not accessible it may be that the ultrasonic transducer would have to be moved through a wall of the high-intensity focused ultrasound system. If the ultrasound transducer is in a position which is allowed for the sonication the mechanical positioning system would then need to be checked to see if the mechanical positioning system can be positioned in an allowed position.

A collision test as used herein encompasses using a geometric model to see if the different geometric components of the geometric model can be positioned without having a collision.

In another embodiment the geometric target region is calculated by the processor executing instructions which cause it to select allowed positions descriptive of the mechanical degrees of freedom of the ultrasound transducer and the mechanical positioning system. Allowed positions are selected from any one of the following: a predetermined list of positions and allowed positions selected using a Monte Carlo Process. This is an alternative embodiment where instead of initially selecting sonication points the achievable target region is determined by placing the mechanical components modeled by the geometric model into allowed positions. This allows an approximate representation of the achievable target region to be determined. A better or improved achievable target region can be used by choosing additional points to move the geometric model into. This is very similar to the process of using a Monte Carlo Process to estimate the area of an integral.

In another embodiment the achievable target region is repeatedly rendered on the display during calculation of the achievable target region. In both of the methods presented the achievable target region is determined or calculated by testing individual points. When just a few points are tested the estimate of the achievable target region is not particularly good. As the number of points which are tested increases the estimate of the achievable target region is gradually increased and becomes better and better. To perform a perfect or a good estimate as is allowed by the model would take prohibitively long. A solution to this is to repeatedly test additional points and then re-render the achievable target region on the display as a better approximation as determined. If the target region is far from the boundary of the achievable target region a rough estimate may suffice. For instance a physician or other operator of the therapeutic apparatus may notice that the target region is well within the boundaries of the achievable target region as it is being calculated. The healthcare professional would then not need to wait to determine if the target region is within the achievable target region or not.

In another embodiment the processor further performs the step of receiving a medical image. The processor further performs the step of rendering the medical image on the display. The geometrical representation of the target region and the achievable target region are superimposed on the medical image. This is particularly advantageous because the relation of the target region and the achievable target region to the anatomy of the subject is easily determined when they are superimposed on the medical image.

In another embodiment the therapeutic apparatus further comprises a magnetic resonance imaging system for acquiring magnetic resonance data. The medical image is received by the processor executing instructions which cause it to acquire the medical image data using the magnetic resonance imaging system. The medical image is further received by the processor executing instructions which cause it to reconstruct magnetic resonance data into the medical image. This embodiment is advantageous because the medical image acquired by the magnetic resonance imaging system may be used to guide the therapy accurately. The medical image may also be registered to the treatment planning data.

In another embodiment the geometric model comprises a tessellated surface model. In a tessellated surface model tessellations or connections like a tile are used to create a surface model. It is advantageous to use a tessellated surface model for the geometric model because the location of tessellated surface models can be accurately calculated by modern processors and computer systems. The geometric model may therefore be used to rapidly calculate the achievable target region.

In another embodiment the geometric model comprises a geometric model of the ultrasound. For example a tessellated surface could be used to represent the path of the ultrasound.

In another embodiment the instructions further cause the processor to generate sonication commands. The sonication of target zone commands as used herein encompass instructions which are performable by the high-intensity focused ultrasound system and which cause the high-intensity focused ultrasound system to perform a sonication or heating of the target region. Execution of the instructions further causes the processor to send the sonication commands to the high-intensity focused ultrasound system. The sending of the sonication commands to the high-intensity focused ultrasound system cause it to perform the sonication or treatment of the target region of the subject.

In another embodiment the processor further performs the step of receiving modifications to the treatment planning data. For instance the processor may execute instructions which cause it to receive data from a graphical user interface on the display. A user could step through different slices and medical image or medical image data and adjust the positioning of the target region. This may be particularly advantageous if the target region is not within the achievable target region.

In another embodiment the processor further performs the step of determining if the achievable target region does not encompass the target region. This is equivalent to determining if the target region is within the achievable target region. If this is the case then the target region is able to be sonicated in its entirety. If not then there may be a region of the target region which is not able to be sonicated. The processor further performs the step of displaying a predetermined message on the display if the achievable target region does not encompass the target region. This may be particularly advantageous because multiple slices or images may be used to represent the target region. This would alert an operator to the fact that part of the target region may not be able to be treated.

In another aspect the invention provides for a computer program product comprising machine executable instructions for execution by a processor. For instance the computer program product may be stored on a computer-readable storage medium. Execution of the instructions causes the processor to receive treatment planning data. The treatment planning data comprises a geometric representation of the target region of a subject. Execution of the instructions further causes the processor to render the geometric representation of the target region on the display. Execution of the instructions further causes the processor to calculate an achievable target region in accordance with a geometric model of a high-intensity focused ultrasound system. The achievable target region is representative of a region treatable by the high-intensity focused ultrasound system. Execution of the instructions further causes the processor to render the achievable target region on a display.

In another aspect the invention provides for a method of rendering achievable target region on a display. The method comprises the step of receiving treatment planning data. The treatment planning data comprises a geometric representation of a target region of a subject. The method further comprises the step of rendering the geometric representation of the target region on a display. The method further comprises the step of calculating an achievable target region in accordance with a geometric model of a high-intensity focused ultrasound system. The achievable target region is representative of a region treatable by the high-intensity focused ultrasound system. The method further comprises the step of rendering the achievable target region on the display.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
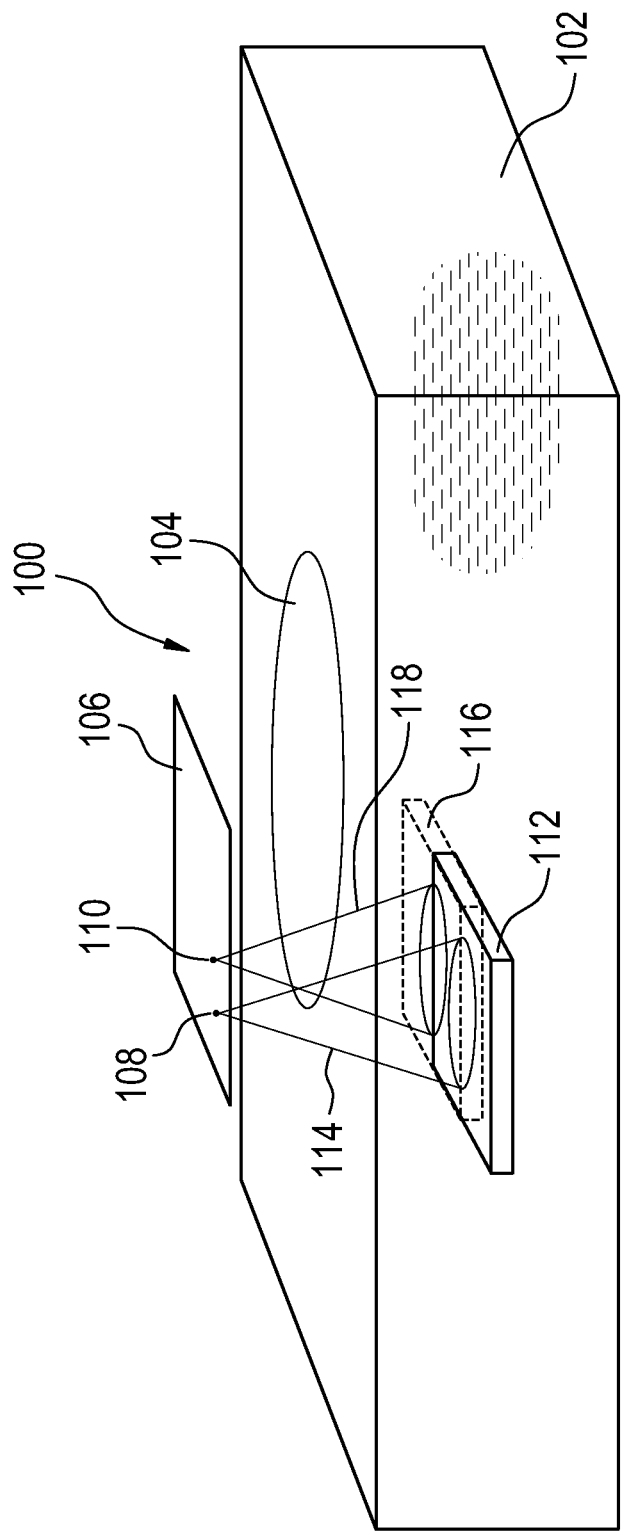
FIG. 1 illustrates a high-intensity focused ultrasound system according to an embodiment of the invention.

FIG. 1 shows a representation of a high-intensity focused ultrasound system 100 according to an embodiment of the invention. The high-intensity focused ultrasound system comprises a fluid-filled chamber 102 which has an ultrasound window 104. The plane labeled 106 is representative of a plane in a subject. Located within plane 106 is a first sonication point 108 and a second sonication point 110. Shown below the sonication points 108, 110 is an ultrasound transducer 112 which is located in a first position. There is a cone 114 which is a geometric model of the ultrasound emitted by the ultrasound transducer 112. It can be seen the point of the cone 114 is placed at the first sonication point 108. The ultrasound transducer is then placed in a first position such that it would generate ultrasound which is represented by the cone 114. The cone 114 can be seen as passing partially through the wall of the fluid-filled chamber 102.

The first sonication point 108 is representative of a sonication point which would not be allowed. The second sonication point 110 has a cone 118 which is representative of ultrasound produced by the ultrasound transducer 116 in a second position. The point of the cone 118 is at the second sonication point 110. It can be seen that the ultrasound 118 passes through the ultrasound window 104. The first sonication point 108 causes a collision and the second sonication point 110 does not cause a collision. The second sonication point 110 would be a member of the achievable target region.

FIG. 1 demonstrates how the achievable target region could be built up by successively testing various sonication points. As the number of sonication points increases the accuracy of the rendered achievable target region would increase.

Figure 2:
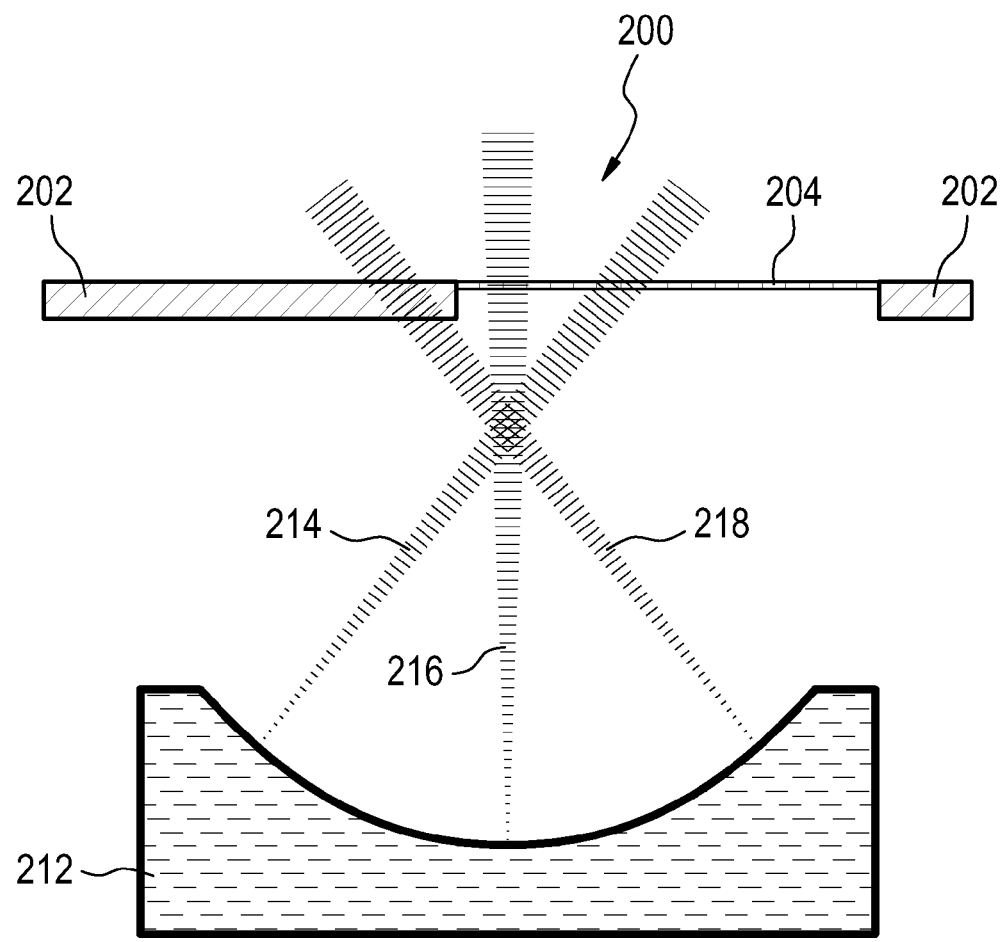
FIG. 2 illustrates a high-intensity focused ultrasound system according to a further embodiment of the invention.

FIG. 2 shows a further representation of a high-intensity focused ultrasound system 200 according to an embodiment of the invention. In this Fig. there is a partial view of a fluid-filled chamber 202 which has an ultrasound window 204. There is an ultrasound transducer 212 located within the fluid-filled chamber 202. The ultrasound transducer 212 in this embodiment is a concave surface which has multiple transducer elements each of which are adapted for emitting ultrasonic energy. To represent this three conical shapes 214, 216, and 218 are drawn to represent ultrasound emitting from three different ultrasonic transducer elements. It can be seen that transducer elements 214 and 216 pass through the ultrasonic window 204. The shape 218 collides or has a collision with the wall of the fluid-filled chamber 202. To reach areas of a subject for which the ultrasound represented by 218 is needed there would be a collision. However, if the ultrasound emitted represented by cone 218 is not needed, then the ultrasonic transducer is usable in this current position. FIG. 2 illustrates how individual shapes representing ultrasound from individual transducer elements can be used to further refine the estimate of the achievable target region.

Figure 3:
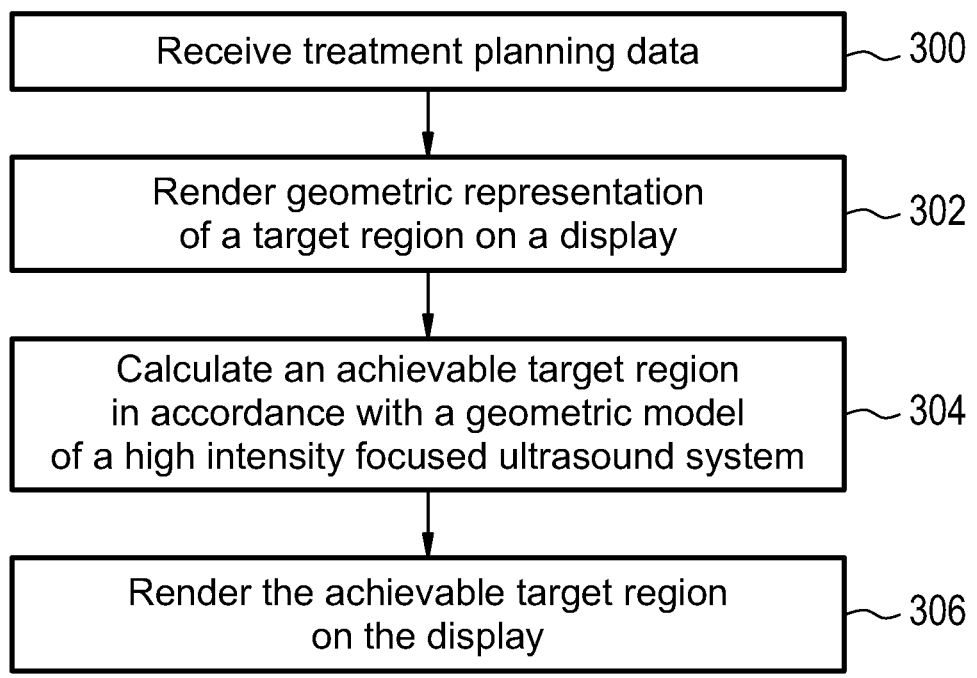
FIG. 3 shows a flow chart which illustrates a method according to an embodiment of the invention.

FIG. 3 shows a flowchart which illustrates a method according to an embodiment of the invention. In step 300 treatment planning data is received. In step 302 a geometric representation of a target area is rendered on a display. The treatment planning data contains the geometric representation of the target area. In step 304 an achievable target region is calculated in accordance with a geometric model on a high-intensity focused ultrasound system. In some embodiments the achievable target region is calculated by approximating it by selecting sonication points or by positioning components of the high-intensity focused ultrasound system to test if a point is either allowed or not allowed or is a member or not a member of the achievable target region. In step 306 the achievable target region is rendered on the display. In this way the target region may be compared to the achievable target region.

Figure 4:
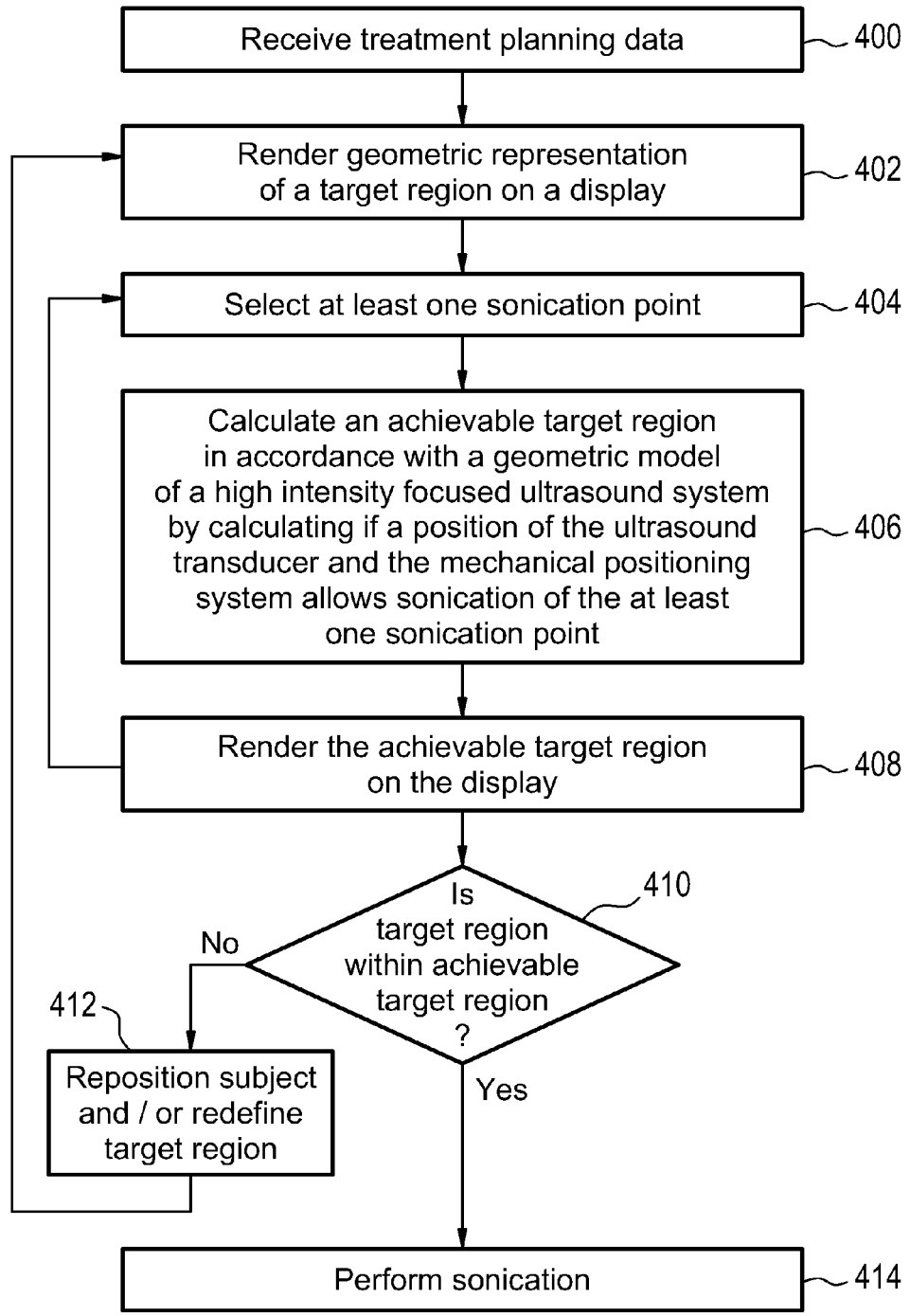
FIG. 4 shows a flow chart which illustrates a method according to a further embodiment of the invention.

FIG. 4 shows a flowchart which illustrates a further method according to an embodiment of the invention. In step 400 treatment planning data is received. Next in step 402 a geometric representation of the target region is rendered on a display. In step 404 the at least one sonication point is selected. Next in step 406 an achievable target region is calculated in accordance with a geometric model of a high-intensity focused ultrasound system by calculating the position of the ultrasound transducer and the mechanical positioning system allow sonication of the at least one sonication point. For instance a collision test may be performed using the geometric model. If there is a collision then the sonication point is not allowed. Next in step 408 the achievable target region is displayed.

The method shown in FIG. 4 also illustrates how this may be an iterative process. After the achievable target region has been rendered on the display there is an arrow which shows that more sonication points are selected and the method goes back to step 404. The achievable target region is recalculated using these additional points and the estimate of the achievable target region is improved. This can be continually improved until a determination is made if the target region is within the achievable target region. This is indicated by decision box 410. If the target region is within the achievable target region then the sonication is performed. This is indicated by step 414. If not then the subject can be repositioned and/or the target region can be redefined. This is indicated by box 412. The method then goes back to step 402 where the geometric representation of the target region is rendered on the display. The method is then repeated until the sonication is performed in step 414.

Figure 5:
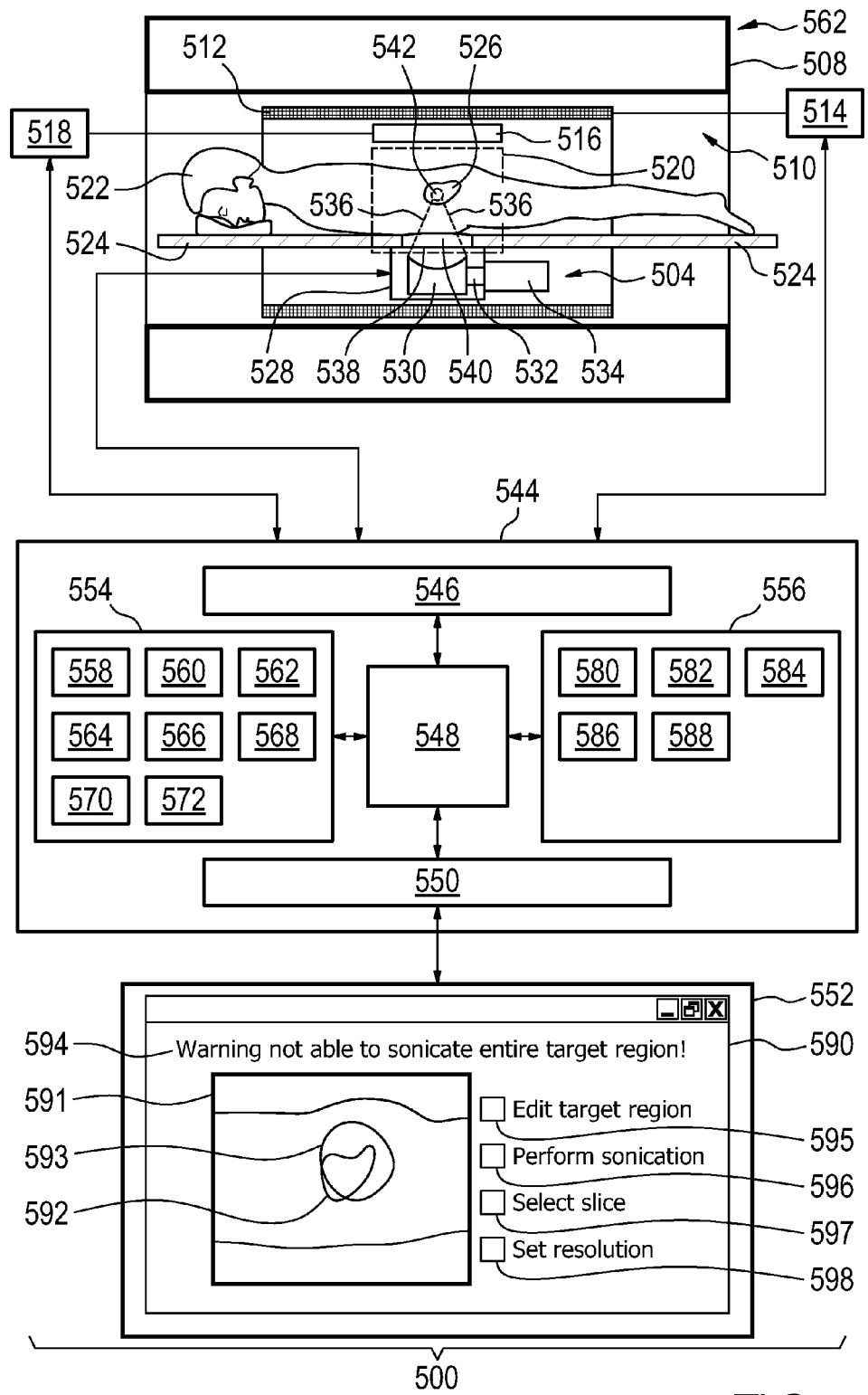
FIG. 5 illustrates a therapeutic apparatus according to an embodiment of the invention.

FIG. 5 shows an embodiment of a therapeutic apparatus 500 according to an embodiment of the invention. The therapeutic apparatus 500 comprises a magnetic resonance imaging system 502 and a high-intensity focused ultrasound system 504. The magnetic resonance imaging system 502 comprises a magnet 508. The magnet shown in FIG. 5 is a cylindrical type superconducting magnet and has a bore 510 through it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

Located within the bore of the magnet 510 is a magnetic field gradient coil 512 which is adapted for acquisition of magnetic resonance data to spatially encode magnetic spins within an imaging zone of the magnet. The magnetic field gradient coil 512 is connected to a magnetic field gradient coil power supply 514. The magnetic field gradient coil 512 is intended to be representative. Typically magnetic field gradient coils contain three separate sets of coils for spatially encoding in three orthogonal spatial directions. A magnetic field gradient power supply 514 supplies current to the magnetic field gradient coils. The current supplied to the magnetic field coils 512 is controlled as a function of time and may be ramped or pulsed.

Also located within the bore of the magnet 510 is a coil 516 or radio frequency antenna which is connected to a transceiver 518. The coil 516 is located adjacent to an imaging zone 520. The imaging zone 520 is a region where the magnetic field created by the magnet 508 is uniform enough for acquiring magnetic resonance imaging data. The coil 516 is for manipulating the orientations of magnetic spins within the imaging zone 520 and for receiving radio transmissions from spins also within the imaging zone. The radio frequency antenna may contain multiple coil elements. The coil may also be referred to as a channel or radio frequency antenna. The radio frequency coil 516 and radio frequency transceiver 518 may be replaced by separate transmit and receive coils and a separate transmitter and receiver. It is understood that the coil 516 and the radio frequency transceiver 518 are simply representative. The coil 516 is intended to also represent a dedicated transmit antenna and a dedicated receive antenna. Likewise the transceiver 518 may also represent a separate transmitter and receivers.

There is a subject 522 reposing on a subject support 524. The subject 522 is partially within the imaging zone 520. There is a target region 526 of the subject 522 which is located within the imaging zone 520. Below the subject support 524 is the high-intensity focused ultrasound system 504.

The high-intensity focused ultrasound system 504 comprises a fluid-filled chamber 528. There is an ultrasound transducer 530 located within the fluid-filled chamber 528. The ultrasound transducer 530 is connected to a mechanical linkage 532 which is adapted for positioning the ultrasound transducer 530 within the fluid-filled chamber 528. There is an actuator 534 which is used for actuating the linkage 532 and is thus able to move and position the ultrasound transducer 530. Not shown in this diagram is a power supply for supplying alternating current electrical power to the ultrasound transducer 530.

The dashed lines 536 show the path of ultrasound generated by the ultrasound transducer 530. The ultrasound 536 passes through the fluid-filled chamber 528 through an ultrasound window 538. Within the subject support 524 is a recession or opening for receiving a gel pad 540. The gel pad is adapted for coupling the ultrasound from the ultrasound window 538 to the subject 522. The gel pad 540 is optional and is not present in all embodiments. The ultrasound 536 is then focused to a sonication volume 542. The sonication volume 542 is shown as being located within the target region 526.

The high-intensity focused ultrasound system 504, the transceiver 518 and the magnetic field gradient coil power supply 514 are all shown as being connected to a hardware interface 546 of a computer system 544. The computer system 544 further comprises a processor 548 which is adapted for sending and receiving signals via the hardware interface 546 for controlling the operation and functioning of the therapeutic apparatus 500. The computer system 544 further comprises a user interface 550. In this embodiment part of the interface 550 is a display 552. The processor 548 is further shown as being connected to computer storage 554 and computer memory 556.

The computer storage 554 is shown as containing magnetic resonance data 558 that was acquired using the magnetic resonance imaging system 502. The computer memory 556 is shown as further containing a magnetic resonance image 560 generated from the magnetic resonance data 558. The computer storage 554 is further shown as containing treatment planning data 562 and a calculated achievable target region 564. The achievable target region 564 is a numerical representation of the achievable target region. Also within the computer memory 556 is a pulse sequence 566 which is used for operating the magnetic resonance imaging system 502. In some embodiments the computer storage 554 contains a predetermined list of sonication test points 568. This list 568 is used during the calculation of the achievable target region 564. The computer storage 554 is shown as containing sonication commands 570 for operating the high-intensity focused ultrasound system 504. The computer storage 554 is shown as containing a geometric model 572 of the components 528, 530, 532 of the high-intensity focused ultrasound system 504.

The computer memory 556 contains computer executable code for execution by the processor 548. The computer memory 556 is shown as containing a control module 580. The control module 580 contains computer executable code for controlling the operation and function of the therapeutic apparatus 500. The computer memory 556 is shown as further containing an image reconstruction module 582. The image reconstruction module contains computer executable code which is used for reconstructing the magnetic resonance image 560 from the magnetic resonance data 558. The computer memory 556 contains a high-intensity focused ultrasound system control module 584 which used the treatment planning data 562 to generate the sonication commands 570. Some embodiments contain a Monte Carlo Module 568 which is used to choose sonication points for determining the achievable target region 564. The computer memory 556 is shown as further containing a collision test module 588. The collision test module 588 contains computer executable code which uses the geometric module 572 to determine if a sonication point is within the achievable target region 546 or not.

Within the display 552 there is a graphical user interface 590. On the graphical interface there is displayed a medical image 591. Superimposed upon the medical image are a target region 592 and an achievable target region 593. In this particular example the target region 592 is not completely within the achievable target region 593. Because the target region 592 is not completely within the achievable target region 593 there is a predetermined message 594 displayed on the graphical user interface 590. The predetermined message 594 warns an operator that the entire target region is not able to be sonicated. The graphical user interface 590 may also contain other control elements for controlling the operation and function of the therapeutic apparatus 500. By way of example there are control buttons 595, 596, 597 and 598. Button 595 is able to open a dialogue which allows the target region to be edited. Button 596 causes the sonication of the target region 526 to begin. This may for instance cause the sonication commands 570 to be sent to the high-intensity focused ultrasound system 504. Button 597 may cause a different slice of medical image to be displayed. The target region 536 is most likely a three-dimensional volume. Therefore the target region may be located on multiple slices of medical image data. The button 598 opens a dialogue box which allows the resolution of the achievable target region to be controlled. For instance to increase the resolution a large number of test sonication points would be selected.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 High Intensity Focused Ultrasound System
102 fluid filled chamber
104 ultrasound window
106 plane in subject
108 first sonication point
110 second sonication point
112 ultrasound transducer (first position)
114 geometric model of ultrasound (first position)
116 ultrasound transducer (second position)
118 geometric model of ultrasound (second position)
200 High Intensity Focused Ultrasound System
202 fluid filled chamber
204 ultrasound window
212 ultrasound transducer
214 cone representing ultrasound
216 cone representing ultrasound
218 cone representing ultrasound
500 therapeutic apparatus
502 magnetic resonance imaging system
504 high intensity focused ultrasound system
508 magnet
510 bore
512 magnetic field gradient coil
514 magnetic field gradient coil power supply
516 coil
518 transceiver
520 imaging zone
522 subject
524 subject support
526 target region
528 fluid filled chamber
530 ultrasound transducer
532 mechanical linkage
534 actuator
536 path of ultrasound
538 ultrasound window
540 gel pad
542 sonication volume
544 computer system
546 hardware interface
548 processor
550 user interface
552 display
554 computer storage
556 computer memory
558 magnetic resonance data
560 magnetic resonance image
562 treatment planning data
564 achievable target region
566 pulse sequence
568 predetermined list of sonication test points
570 sonication commands
572 geometric model
580 control module
582 image reconstruction module
584 high intensity focused ultrasound system control module
586 Monte Carlo module
588 collision test module
590 graphical user interface
591 medical image
592 target region
593 achievable target region
594 predetermined message
595 edit target region button
596 perform sonication button
597 select slice button
598 set resolution button

The invention claimed is:

1. A therapeutic apparatus comprising:
a high intensity focused ultrasound system for treating a target region of a subject;
a processor for controlling the therapeutic system;
a display for displaying treatment planning data;
a memory containing machine executable instructions for execution by the processor, wherein the memory further contains a geometric model including at least a two-dimensional geometric representation of the path of the high intensity focused ultrasound system, wherein execution of the instructions causes the processor to:
receive the treatment planning data, wherein the treatment planning data comprises a geometric representation of the target region;
render the geometric representation of the target region on the display;
calculate an achievable target region in accordance with the two-dimensional geometric representation of the path, wherein the achievable target region is representative of at least a two-dimensional region treatable by the high intensity focused ultrasound system; and
render the achievable target region on the display.

2. The therapeutic apparatus of claim 1, wherein the high intensity focused ultrasound system comprises an ultrasound transducer, wherein the high intensity focused ultrasound system further comprises a mechanical positioning system, wherein the geometric model further includes a model of the mechanical positioning system.

3. The therapeutic apparatus of claim 2, wherein the geometric model comprises a three-dimensional geometric representation of the path of focused ultrasound generated by the ultrasound transducer.

4. The therapeutic apparatus of claim 2, wherein the achievable target region is calculated by execution of the instructions which further cause the processor to:
select at least one sonication point;
calculate if a position of the ultrasound transducer and the mechanical positioning system allows sonication of the at least one sonication point in accordance with the geometric model including the two-dimensional geometric representation of the path and the model of the mechanical positioning system.

5. The therapeutic apparatus of claim 4, wherein the allowance of sonication is tested using a collision test in accordance with the geometric model including the two-dimensional geometric representation of the path and the model of the mechanical positioning system.

6. The therapeutic apparatus of claim 4, wherein the at least one sonication point is selected using any one of the following: a predetermined list or a Monte Carlo process.

7. The therapeutic apparatus of claim 4, wherein the achievable target region is calculated by execution of the instructions which further cause the processor to select allowed positions descriptive of the mechanical degrees of freedom of the ultrasound transducer and the mechanical positioning system, and wherein the allowed positions are selected from any one of the following: a predetermined list of positions and allowed positions selected using a Monte Carlo process.

8. The therapeutic apparatus of claim 1, wherein the achievable target region is repeatedly rendered on the display during the calculation of the achievable target region.

9. The therapeutic apparatus of claim 1, wherein the processor further performs the steps of:
receiving a medical image; and
rendering the medical image on the display, wherein the geometrical representation of the target region and the achievable target region are superimposed on the medical image.

10. The therapeutic apparatus of claim 9, wherein the therapeutic apparatus further comprises a magnetic resonance imaging system for acquiring magnetic resonance data, wherein the medical image is received by executing the instructions which further cause the processor to:
acquire the medical image using the magnetic resonance imaging system,
reconstruct the magnetic resonance data into the medical image.

11. The therapeutic apparatus of claim 1, wherein the geometric model comprises a two-dimensional tessellated surface model representation of the path of the high intensity focused ultrasound system.

12. The therapeutic apparatus of claim 1, wherein execution of the instructions further cause the processor to:
generate sonication commands; and
send sonication commands to the high intensity focused ultrasound system.

13. The therapeutic apparatus of claim 1, wherein the processor further performs the steps of:
determining if the achievable target region does not encompass the target region; and
displaying a predetermined message on the display if the achievable target region does not encompass the target region.

14. A non-transitory computer program product comprising machine executable instructions for execution by a processor; wherein execution of the instructions causes the processor to:
receive treatment planning data, wherein the treatment planning data comprises a geometric representation of a target region of a subject;
render the geometric representation of the target region on the display;
calculate an achievable target region in accordance with a geometric model including at least a two-dimensional geometric representation of the path of a high intensity focused ultrasound system, wherein the achievable target region is representative of at least a two-dimensional region treatable by the high intensity focused ultrasound system; and
render the achievable target region on a display.

15. A method of rendering an achievable target region, the method comprising:
a processor coupled to a display and configured to perform acts of:
receiving treatment planning data, wherein the treatment planning data comprises a geometric representation of a target region of a subject;
rendering the geometric representation of the target region on the display;
calculating an achievable target region in accordance with a geometric model including at least a two-dimensional geometric representation of the path of a high intensity focused ultrasound system, wherein the achievable target region is representative of at least a two-dimensional region treatable by the high intensity focused ultrasound system; and
rendering the achievable target region on the display.

* * * * *